US00PP23295P2

(12) United States Plant Patent
Egger

(10) Patent No.: US PP23,295 P2
(45) Date of Patent: Jan. 1, 2013

(54) ***TRADESCANTIA* PLANT NAMED 'ANGELIC CHARM'**

(50) Latin Name: ***Tradescantia Andersoniana* Group**
Varietal Denomination: Angelic Charm

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/200,414

(22) Filed: Sep. 22, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para

(74) *Attorney, Agent, or Firm* — Klarquist Sparkman, LLP

(57) ABSTRACT

A new and distinct cultivar of *Tradescantia* plant characterized by yellow gold to yellow green foliage, white flowers, a compact clumping habit, and excellent vigor.

1 Drawing Sheet

Botanical denomination: *Tradescantia Andersoniana* Group.

Variety designation: 'Angelic Charm'.

BACKGROUND OF THE INVENTION

The present invention relates to a new and distinct cultivar of *Tradescantia*, given the name, 'Angelic Charm'. *Tradescantia* is in the family Commelinaceae. This new variety is from a planned breeding cross for yellow foliage, compact *Tradescantia*. The new cultivar is a seedling from the cross of *Tradescantia* 27-1, a proprietary, unnamed seedling, as the seed parent and *Tradescantia* 28-3 another proprietary, unnamed seedling, as the pollen parent. Compared to the seed parent, *Tradescantia* 27-1, the new cultivar has white flowers rather than blue. Compared to the pollen parent, *Tradescantia* 28-3, the new cultivar has yellow gold to yellow green foliage rather than green foliage. Compared to *Tradescantia* 'Blue and Gold' (syn. 'Sweet Kate'), the new cultivar has white rather than blue flowers and has a more compact habit.

SUMMARY OF THE INVENTION

This plant exhibits the following characteristics that make it unique:

1. yellow gold to yellow green foliage,
2. white flowers,
3. a compact clumping habit, and
4. excellent vigor.

The new variety has been reproduced only by asexual propagation (division and micropropagation). Each of the progeny exhibits identical characteristics to the original plant. Asexual propagation by division and micropropagation using terminal and lateral buds as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old *Tradescantia* 'Angelic Charm' growing in a one gallon container outside in full sun in late July in Canby, Oreg.

DETAILED PLANT DESCRIPTION

The following is a detailed description of the new *Tradescantia* cultivar based on observations of one-year-old specimens grown in a 1 gallon container in the greenhouse in May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Upright.
*Type*.—Herbaceous perennial.
*Cold hardiness*.—USDA Zone 4-9.
*Size*.—Grows to 55 cm wide and 32 cm tall to the top flowers.
*Vigor*.—Excellent.
*Stem*.—Oval in cross section, swollen at nodes and leafy, grows to 10 mm wide and 30 cm tall, glabrous, internodes range from 8 to 12 cm long, Yellow Green 146B.
*Roots*.—Thick and fleshy, plants root easily from nodes or crown division.

Leaf:

*Type*.—Simple.
*Arrangement*.—Spiral.
*Shape*.—Linear-lanceolate.
*Venation*.—Parallel.
*Leaf description*.—Sessile, grows to 36 cm long and 19 mm wide, margins entire except near base where villous, glabrous on top and bottom, tip acuminate, base perfoliate.
*Leaf color*.—Varies with light, top and bottom side, ranges from Yellow Green 145B near the tip to Yellow Green 146A at the base; more yellow if grown in full sun.

Inflorescence:

*Type*.—Terminal umbel-like cyme subtended by 1 or 2 leafy bracts (smaller than the leaves, otherwise the similar, grow to 12 cm long, 20 mm wide, linear to linear lanceolate, top and bottom side Yellow Green 145B).

*Number of flowers per cyme*.—Up to 35.

*Size of inflorescence*.—4 cm tall and 4.5 cm wide.

*Peduncle*.—None.

*Pedicel*.—Grows to 18 mm long and 1 mm wide, glabrous, flattened, Grey Brown 199D in shade to Purple Violet N81A in sun.

*Bloom period*.—Late May through July in Canby, Oreg.

Flower bud:

*Size*.—10 mm long and 6 mm wide at the widest point prior to opening.

*Description*.—Ovoid.

*Surface texture*.—Pubescent.

*Color*.—Yellow Green 144D.

Flower:

*Type*.—Actinomorphic to irregular, single.

*Size*.—40 mm wide and 15 mm deep.

*Corolla description*.—3 petals, each broadly ovate in shape, sometimes somewhat pleated at the midrib, 20 mm wide and 21 mm long, margin entire, tip obtuse, base attenuate, glabrous on both sides, top and bottom side White NN155D.

*Calyx description*.—3 sepals, 10 mm long and 6 mm wide, pubescent outside and glabrous inside, ovate, cupped, margin entire, tip acute, Yellow Green 146C on both sides.

*Pistil description*.—1 in number, 10 mm long, ovary 2 mm long, Yellow Green 145C, style 8 mm long, White NN155D; stigma White NN155D.

*Stamen description*.—6 in number, 8 mm long, filaments 7 mm long, White NN155D with long White NN155D hairs on bottom ⅔, anthers reniform in shape, 0.5 mm long, Yellow 13A, pollen slight, Yellow 13A.

*Fragrance*.—None.

*Lastingness*.—A cyme blooms for about 4 weeks on the plant.

Fruit/seed: Fruit a 3-valved, 3-loculed capsule, 1 seed found for 50 flowers, extremely low fertility, seeds oval, 5 mm long and 3 mm wide, Black 202A.

Pests and diseases: *Tradescantia Andersoniana* Group is known to be susceptible viruses, aphids, and spider mites. The new cultivar has no known resistances but has shown no problems in Canby, Oreg.

I claim:

1. A new and distinct form of *Tradescantia* plant as shown and described herein.

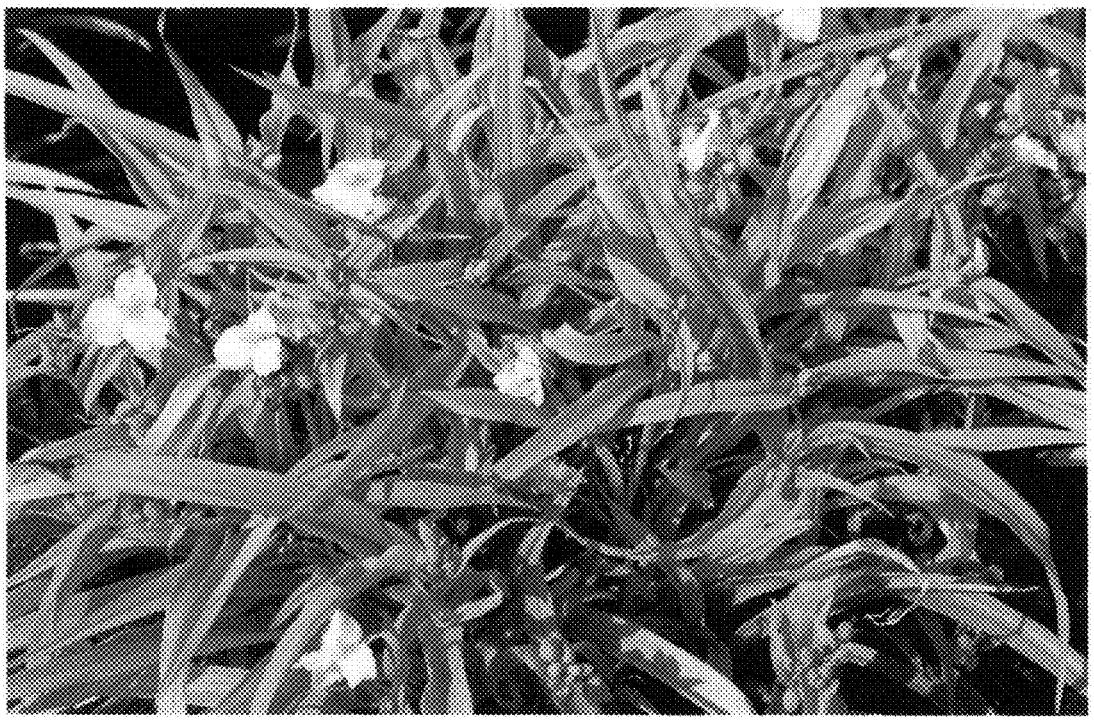

* * * * *